US00RE38776E

(19) United States
(12) Reissued Patent
Bauer

(10) Patent Number: US RE38,776 E
(45) Date of Reissued Patent: Aug. 16, 2005

(54) SURGICAL BIOPSY INSTRUMENT

(75) Inventor: Alberto Bauer, Cento (IT)

(73) Assignee: Allegiance Corporation, McGaw Park, IL (US)

(21) Appl. No.: 09/655,637

(22) Filed: Dec. 14, 2000

Related U.S. Patent Documents

Reissue of:
(64) Patent No.: 5,313,958
Issued: May 24, 1994
Appl. No.: 08/051,649
Filed: Apr. 22, 1993

(51) Int. Cl.[7] ..... A61B 10/00
(52) U.S. Cl. ..... 600/567; 600/564; 606/170
(58) Field of Search ..... 600/562, 564–567; 606/167, 170

(56) References Cited

U.S. PATENT DOCUMENTS 3,995,619 A * 12/1976 Glatzer et al. ..... 128/754
4,600,014 A * 7/1986 Beraha ..... 128/754
5,156,160 A * 10/1992 Bennett ..... 128/754
5,172,702 A * 12/1992 Leigh et al. ..... 128/754

* cited by examiner

*Primary Examiner*—Charles A. Marmor, II
(74) *Attorney, Agent, or Firm*—Paul E. Schaafsma; Andrew G. Rozycki

(57) ABSTRACT

A surgical instrument in the form of a biopsy needle for removing tissue samples from a patient. The device has means for preloading to excise tissue samples of a preselected one of many possible tissue sample sizes. After preloading, the procedure is easily accomplished using a single hand. The tip is rendered less traumatic by positioning the distal end of the tissue sample notch relatively close to the very distal tip of the stylet. This is accomplished by grinding the distal tip of the stylet into an elliptical shape in a plane having a lateral projection which is away from the distal end of the tissue sample notch.

6 Claims, 8 Drawing Sheets

SURGICAL BIOPSY INSTRUMENT

Matter enclosed in heavy brackets [ ] appears in the original patent but forms no part of this reissue specification; matter printed in italics indicates the additions made by reissue.

BACKGROUND OF THE INVENTION

1. Summary of the Invention

The present invention generally relates to medical devices and more particularly relates to surgical instruments.

2. Description of the Prior Art

The diagnostic advantages of obtaining and analyzing a tissue sample have been long known. This procedure is often termed biopsy. To be most useful, the surgical instrument or biopsy needle, utilized to obtain the tissue sample must be insertable through the skin of the patient, guidable through the body to the sample site, and capable of quickly and easily excising and removing the selected sample.

An early biopsy instrument is seen in U.S. Pat. No. 3,577,979, issued to van der Gaast, incorporated herein by reference. Called a disposable surgical skin punch by the inventor, the device is capable of taking manual core samples. U.S. Pat. No. 4,940,061, issued to Terwilliger et al., incorporated herein by reference, shows an extremely complex motorized version of a biopsy instrument. Though probably somewhat easier to operate, the cost of manufacturing such a device probably precludes disposable use, which has become a major health care consideration. Unlike the earlier device, Terwilliger et al. employs a stylet having a tissue notch concentrically slidable within a sharpened canula. This basic sampling technique has become the standard technique.

To facilitate maintenance of the tissue excising portion of the needle, U.S. Pat. No. 5,031,634, issued to Simon and incorporated herein by reference, shows the use of retractable barbs at the distal end. This may be particularly adapted to soft tissue use, particularly the breast. U.S. Pat. No. 5,036,860, issued to Leigh et al., incorporated herein by reference, shows a device especially intended to be disposable following single use. With the increasing awareness of blood borne viruses, disposability is now a key feature.

U.S. Pat. No. 5,125,413, issued to Baran and incorporated herein by reference, describes a spring loaded device permitting single hand operation by attending medical personnel. Before use, the spring is compressed providing retraction of the outer canula proximally of the distal stylet tip. The distal end of the instrument is advanced to the sample site. Releasing the spring advances the sharpened canula over the stylet thus excising the tissue sample within the sample notch (see FIG. 9). This has become the typical method for biopsy procedures. Alternative tissue notch configurations are shown in U.S. Pat. No. 5,127,419, issued to Kaldany.

SUMMARY OF THE INVENTION

The present invention overcomes the disadvantages found in the prior art devices by providing a convenient means for adjusting length of the core sample taken along with a less traumatic approach, which does not require excess distal extension of the needle beyond the tissue sample site.

To provide an adjustable length core sample, the tissue sample notch is relatively large in the longitudinal direction. However, the canula is retracted exposing the entire length of the tissue sample notch only when taking the largest tissue sample. For smaller tissue samples, the canula is only partially retracted to expose only a portion of the tissue sample notch. In the preferred mode of the present invention, two or three different tissue sample sizes are provided. To accomplish this, the canula may be retracted to one of two or three different positions, with the spring being adequately compressed at each. Release of the spring drives the sharpened canula distally excising and capturing a tissue sample having the corresponding one of the three possible sizes.

The biopsy needle is rendered less traumatic by restricting the distance between the most distal point of the stylet and the most distal face of the tissue sample notch. This means that the stylet need be advanced only slightly beyond the intended sample to accommodate the distal tip (i.e. the distance between the distal tip and the most distal face of the tissue sample notch). Rigidity and strength of the distal end of the stylet ar enhanced by grinding the point at the tip of the stylet in a plane having a lateral projection on the longitudinal axis of the stylet which is away from the location of the tissue sample notch. The canula is similarly ground to provide even greater assurance of tip stability.

The resulting biopsy needle is a precision surgical instrument providing readily adjustable tissue sample size and atraumatic insertion, which is disposable after a single use. The attending personnel preload the canula for one of the two or three tissue sample sizes before use, thereby compressing the spring. Using the convenient finger holders, the instrument is inserted into the patient's body and advanced to the sample site by single handed control of the surgeon. The stylet is advanced through the sample site to present the tissue sample to the tissue sample notch. The canula is released, and the compressed spring advances the canula over the tissue sample notch of the stylet, thus excising the tissue sample. The instrument containing the tissue sample is removed from the patient.

BRIEF DESCRIPTION OF THE DRAWINGS

Other objects of the present invention and many of the attendant advantages of the present invention will be readily appreciated as the same becomes better understood by reference to the following detailed description when considered in connection with the accompanying drawings, in which like reference numerals designate like parts throughout the figures thereof and wherein.

DETAILED DESCRIPTION OF THE PREFERRED EMBODIMENTS

Figure 1:
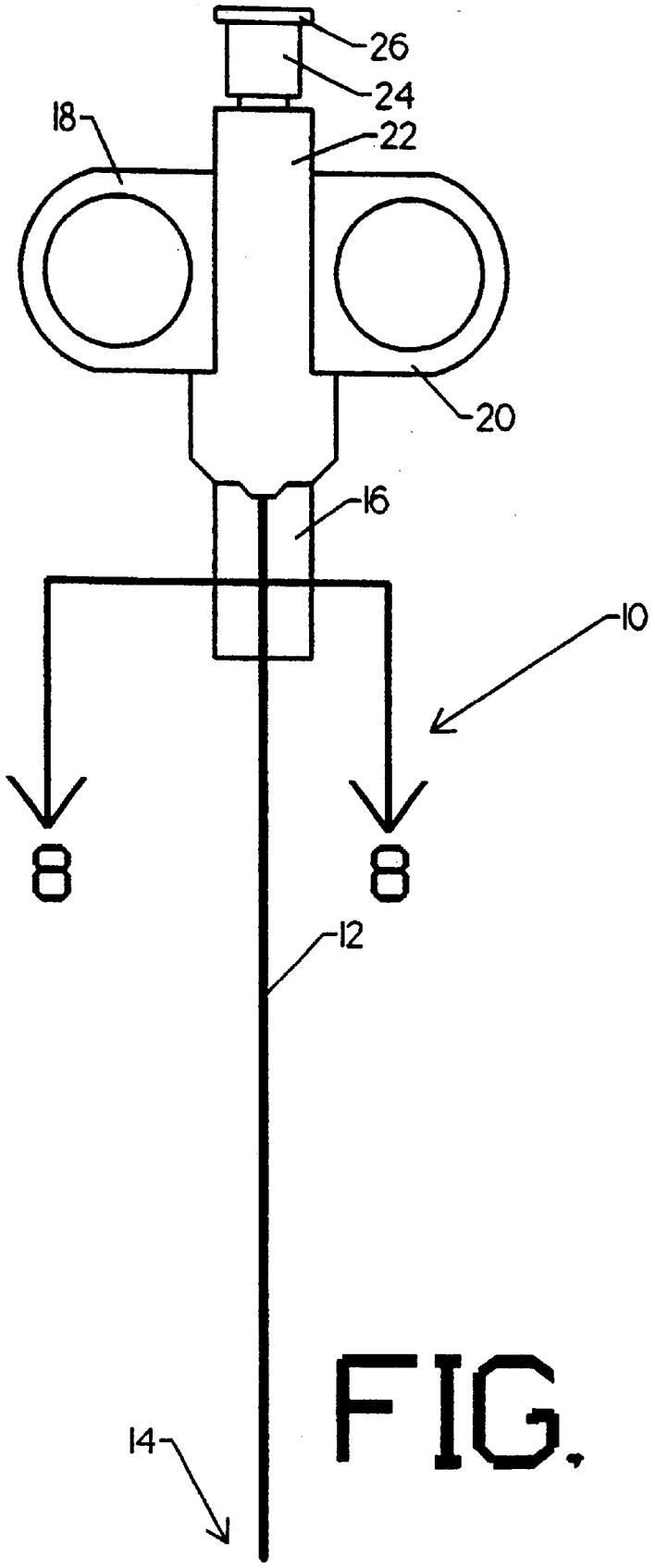
FIG. 1 is a plan view of a surgical instrument employing the present invention.

FIG. 1 is a frontal plan view of a surgical instrument, often called biopsy needle, made and used in accordance with the preferred mode of the present invention. Those of skill in the art will be readily able to apply the teachings found herein to yet other embodiments within the scope of the present invention.

To be inserted into the patient is long thin stainless steel canula 12. Although not seen in this view, canula 12 is hollow, having a central lumen containing a longitudinally slidable stylet which is described in greater detail below. Of particular interest is distal tip 14 which is also described in greater detail below and shown in close up in FIG. 6.

The proximal end of canula 12 is coupled to preloading engagement assembly 16 to permit retraction and advancement of canula 12 with respect to main housing 22, which are preferably molded of a suitable polymer for disposability. Before insertion, the surgical instrument is preloaded by manually pulling actuation button 24 proximally of main housing 22 until engagement of the preloading engagement assembly 16 is achieved for the desired tissue sample size.

The preloaded surgical instrument 10 is grasped by the attending medical person using a single hand. The index finger is placed in finger hold 20 and the middle finger is placed in finger hold 18. Distal tip is advanced into the patient to the tissue sample site. After distal tip 14 is located at the tissue sample site, thumb surface 26 is pressed to carefully advance actuation button 24 distally. This is done carefully to avoid applying sufficient force to disengage preloading engagement assembly 16. This advances the distal tip of the stylet (not shown), which passes through grommet 28, past the tissue sample site exposing the tissue sample notch of the selected size (i.e. size preloaded). Further pressure is exerted on thumb surface 26 to disengage preloading engagement assembly 16. This permits the spring (not shown), which was compressed during the preloading procedure, to drive the sharpened distal tip of canula 12 in the distal direction to excise the tissue sample and encase it between the tissue sample notch and the inner wall of canula 12. Surgical instrument 10 is removed, and the tissue sample it contains is removed and analyzed.

Figure 2:
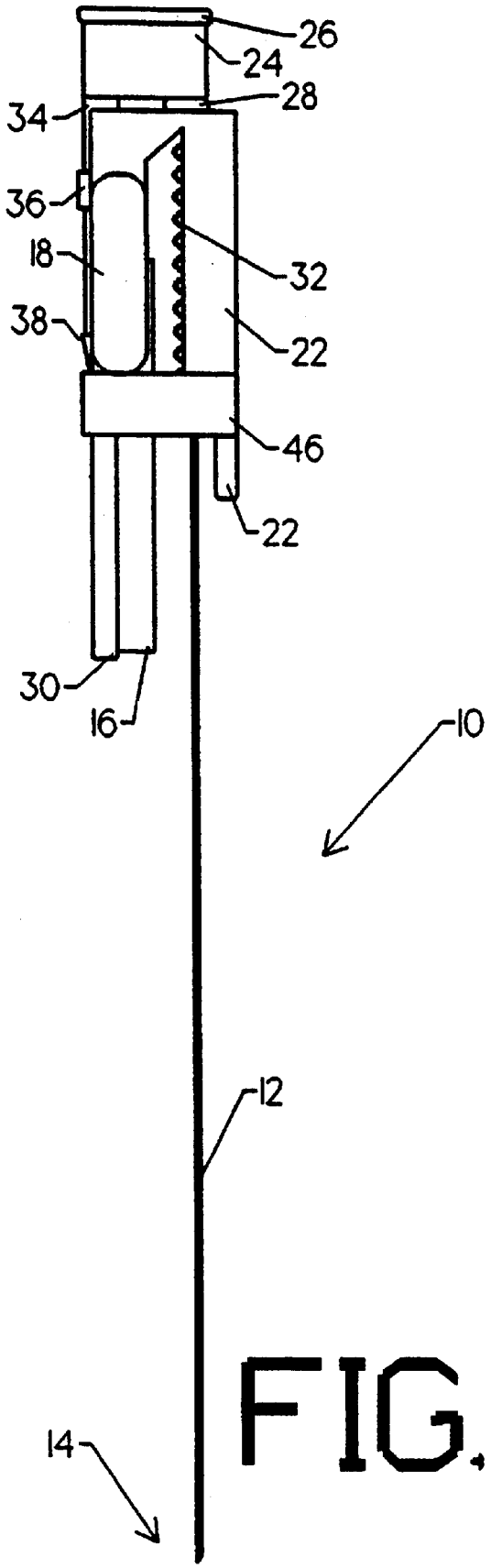
FIG. 2 is a side view of the surgical instrument of FIG. 1.

FIG. 2 is a side view of surgical instrument 10. Preloading engagement assembly 16 is slidably contained within engagement track 30, which is fixedly attached and preferably molded as part of housing 22. A tab of preloading engagement assembly 16, obscured in the view by fixed strut 46 and housing 22, is fixedly coupled to the proximal end of canula 12 and impinges on the distal end of compression spring 32. Therefore, as preloading engagement assembly 16 slides proximally within engagement track 30, canula 12 moves in a proximal direction and compression spring 32 is further compressed.

During the preloading procedure, actuation button 24 is pulled proximally with regard to housing 22. As a result, preloading engagement assembly 1 is pulled proximally within engagement track 30 by preloading strut 34. In accordance with the above explanation, this tends to further compress compression spring 32 and to move canula 12 in a proximal direction. Engagement latch 38 latches preloading engagement assembly 16 in one of many possible positions (i.e. selections of the tissue sample size). Compression spring 32 tends to keep preloading engagement assembly 16 in the selected position by the distal force of its compression. Fixed strut 36, which is preferably molded as a portion of housing 22, maintains the position of preloading strut 34.

Figure 3:
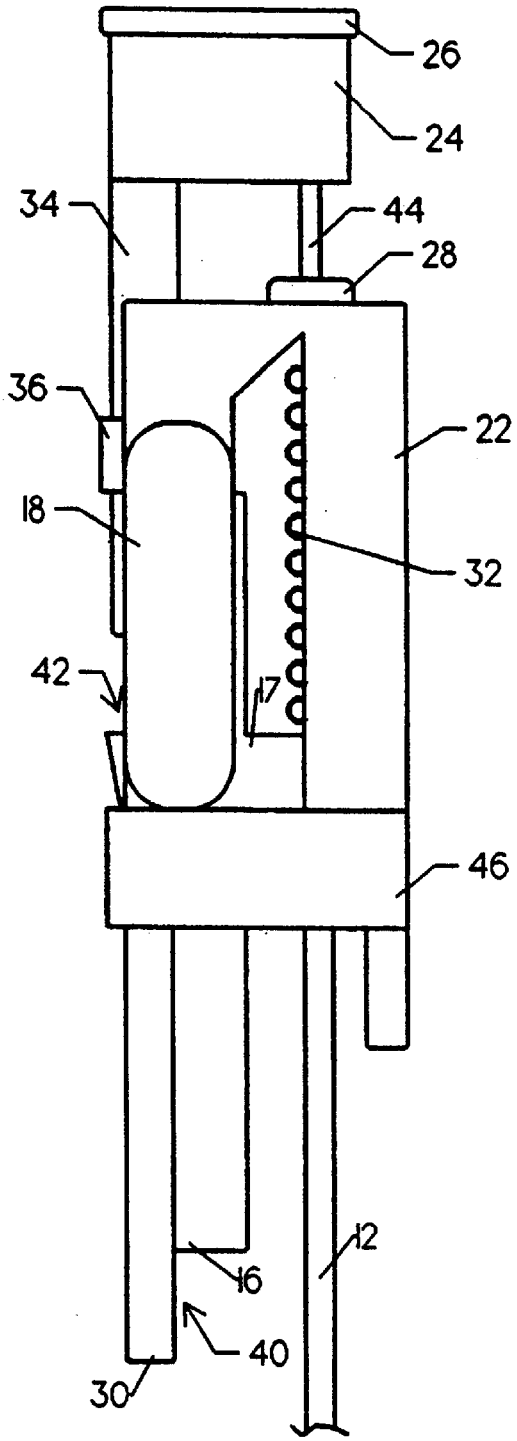
FIG. 3 is a partial side view preloaded for the smallest tissue sample size.

FIG. 3 is a partial side view showing surgical instrument 10 preloaded for the smallest tissue sample size. Preloading engagement assembly 16 has been slid proximally the distance 40, exposing a partial view of tab 17, which is preferably molded as a portion of preloading engagement assembly 16. It is latched by engagement latch 38 at corresponding distance 42. In the preloaded state, the proximal end of stylet 44 can be seen protruding from grommet 28 and attached to actuation button 24. All other referenced elements are as previously described.

Figure 4:
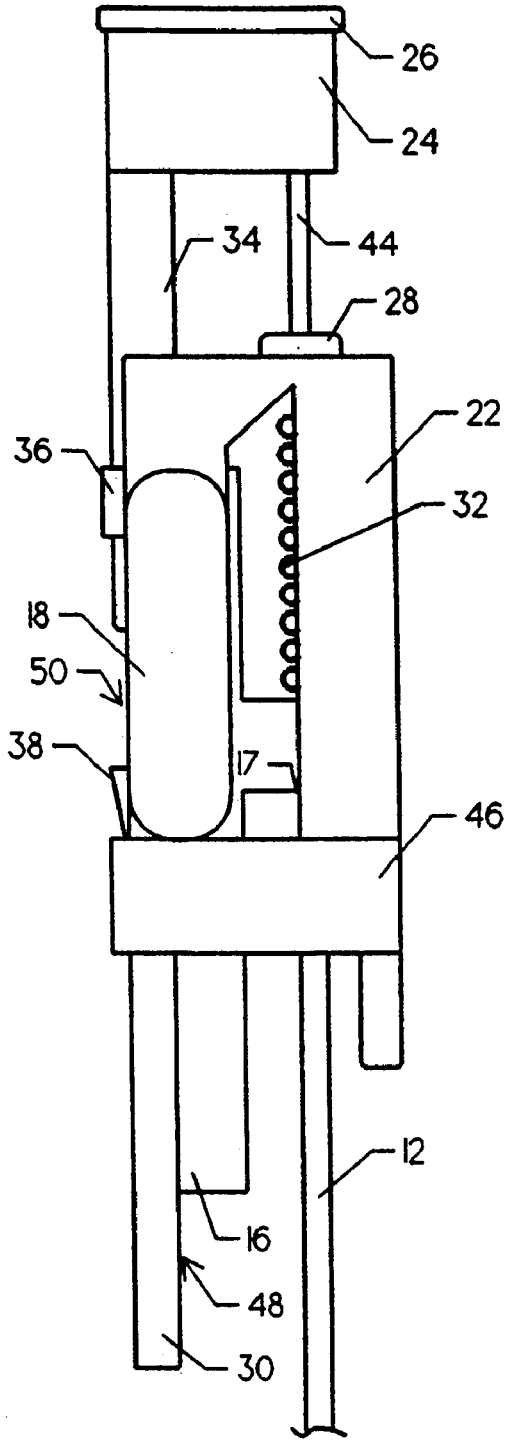
FIG. 4 is a partial side view preloaded for the intermediate tissue sample size.

FIG. 4 is a partial side view, similar to FIG. 3, showing surgical instrument 10 preloaded to an intermediate tissue sample size. Distance 48 is greater than distance 40 (see also FIG. 3) and directly corresponds to distance 50. Also show is a larger view of tab 17 of preloading engagement assembly 16.

Figure 5:
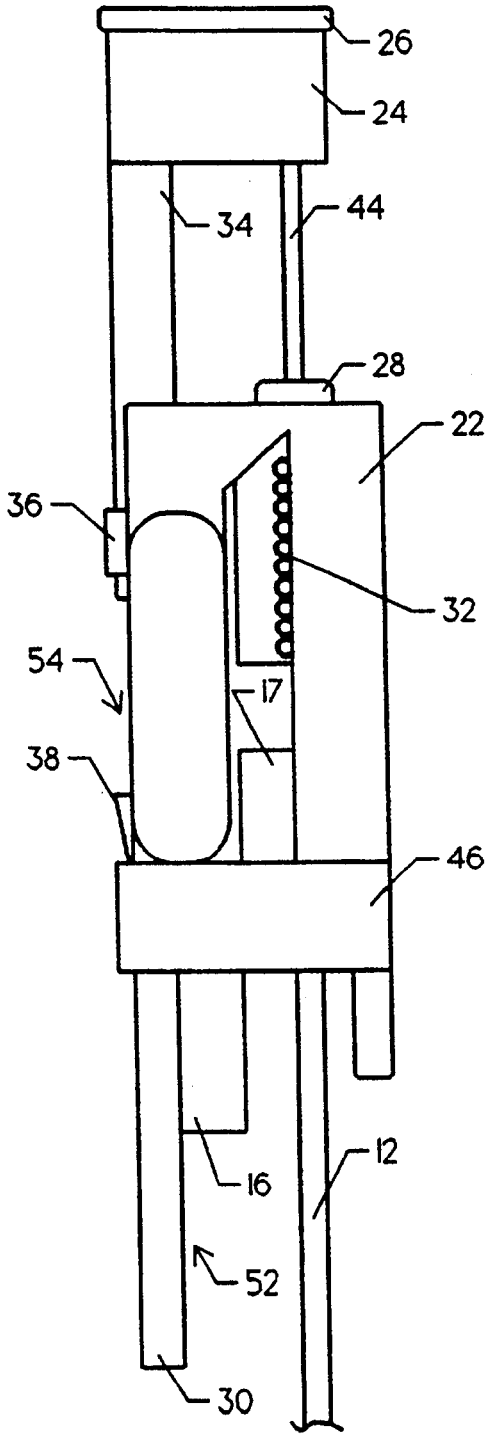
FIG. 5 is a partial side view preloaded for the largest tissue sample size.

FIG. 5 is a partial side view, similar to FIG. 4, showing surgical instrument 10 preloaded to the largest tissue sample size. Distances 52 and 54 are at a maximum. All other referenced elements are as previously described.

Figure 6:
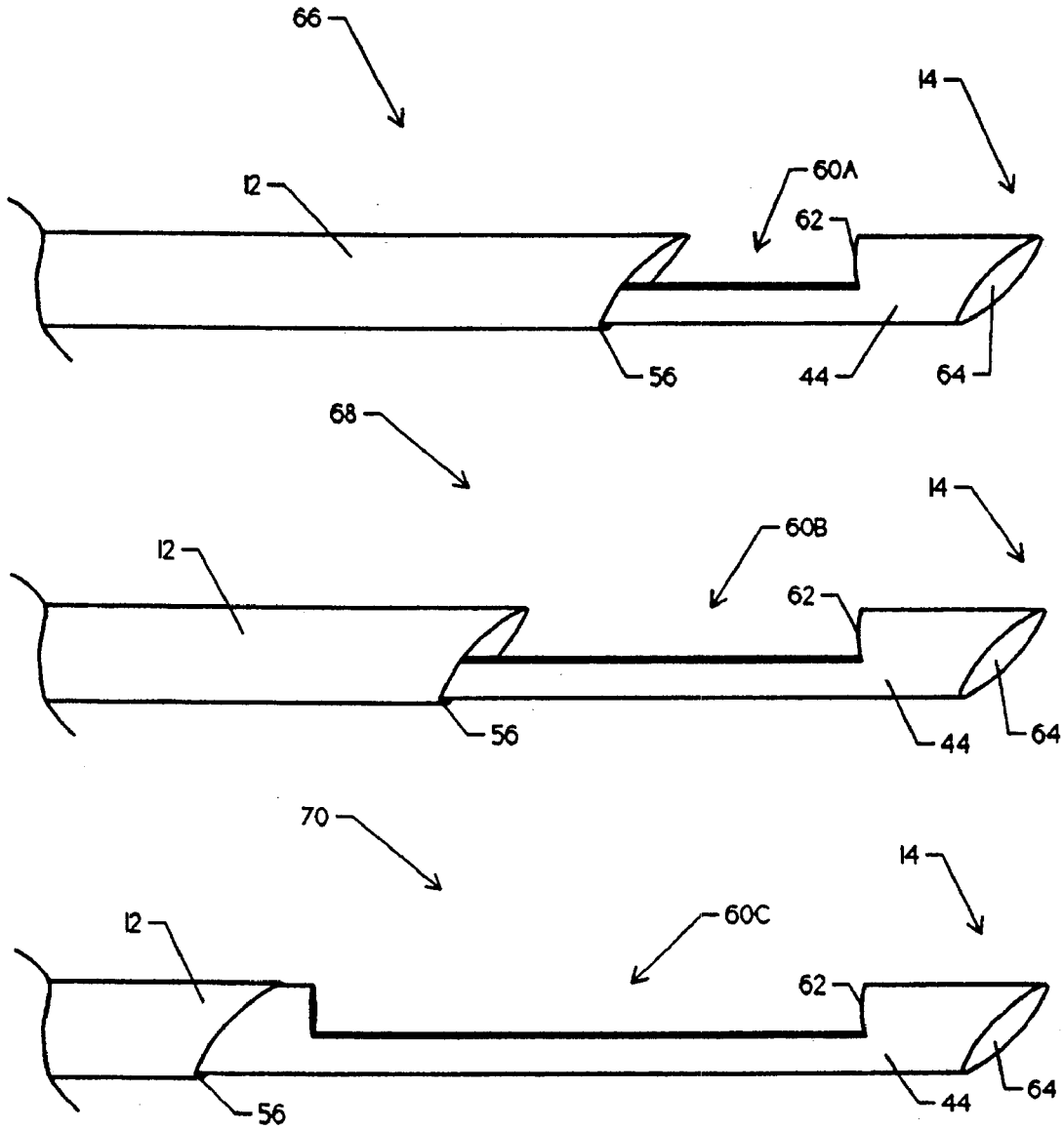
FIG. 6 is a cut away close up view of the distal tip showing the tissue sample notch preloaded for the three different tissue sample sizes.

FIG. 6 shows three close up view of distal tip 14. View 66 corresponds to preloading of the device for the smallest tissue sample size 60A with stylet 44 advanced to the distal most position for exposure of the tissue sample notch.

View 68 shows stylet 44 advanced distally after preloading to intermediate tissue sample size 60B. Similarly, view 70 shows largest tissue sample size 60C.

For each of these configurations, the tissue sample present within the tissue sample notch is excised by sharpened edge 56 of canula 12 as compression spring 32 drives canula 12 distally over stylet 44 upon disengagement of preloading engagement assembly 16 (see also FIGS. 1–5). In the completely disengaged position, canula 12 preferably covers stylet 44 completely, thus encasing the excised tissue sample.

In the preferred embodiment, distal end 64 of stylet 44 is ground to an elliptical shape in a plane directed away from distal end 62 of the tissue notch. This permits the distance from distal edge 62 to the most distal point of stylet 44 to be minimized for a given rigidity of the distal end of stylet 44, because it maximizes the distance from distal edge 62 to distal end 64. Minimizing the distance from distal edge 62 to the most distal point of stylet 44 tends to limit the trauma to the patient because it minimizes the distance beyond the tissue sample which must be pierced by stylet 44 (i.e. the distance from distal end 62 to the most distal point of distal end 64). Further rigidity is achieved by grinding sharpened edge 56 in the same plane as distal end 64.

Figure 7:
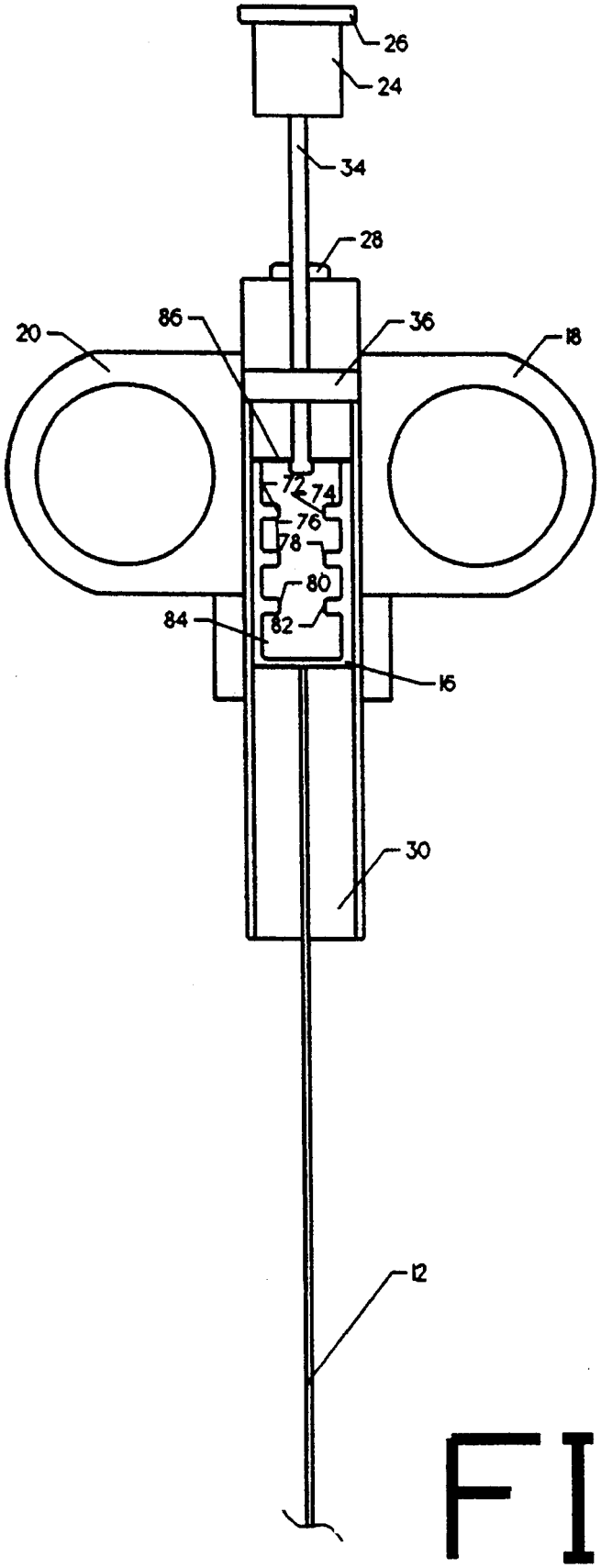
FIG. 7 is a partially cut away rear view showing the means for preloading for different tissue sample sizes.

FIG. 7 is a rear view of surgical instrument 10 preloaded to the largest tissue sample size with engagement latch 38 and a portion of engagement track 30 removed to show details of preloading engagement assembly 16. A portion of the rear of preloading engagement assembly 16 is concavely recessed creating general recess 84. This recess permits advancement of engagement strut 34 distally to advance stylet 44 distally of canula 12 to expose the tissue sample notch to the tissue sample (see also FIG. 6). However, proximal movement of engagement strut 34 engages preloading stop 86 to permit preloading.

General recess 84 contains stop members 72 and 74 for the smallest tissue sample size; stop members 76 and 78 for the intermediate tissue sample size; and stop members 80 and 82 for the largest tissue sample size. These stop members latch against engagement latch 38 (see also FIG. 3–5) to maintain the preselected tissue sample size. However, engagement strut 34 is free to move distally of stop members 72, 74, 76, 78, 80, and 82 within general recess 84 to permit advancement of stylet 44 distally of canula 12 (see also FIG. 6).

Figure 8:
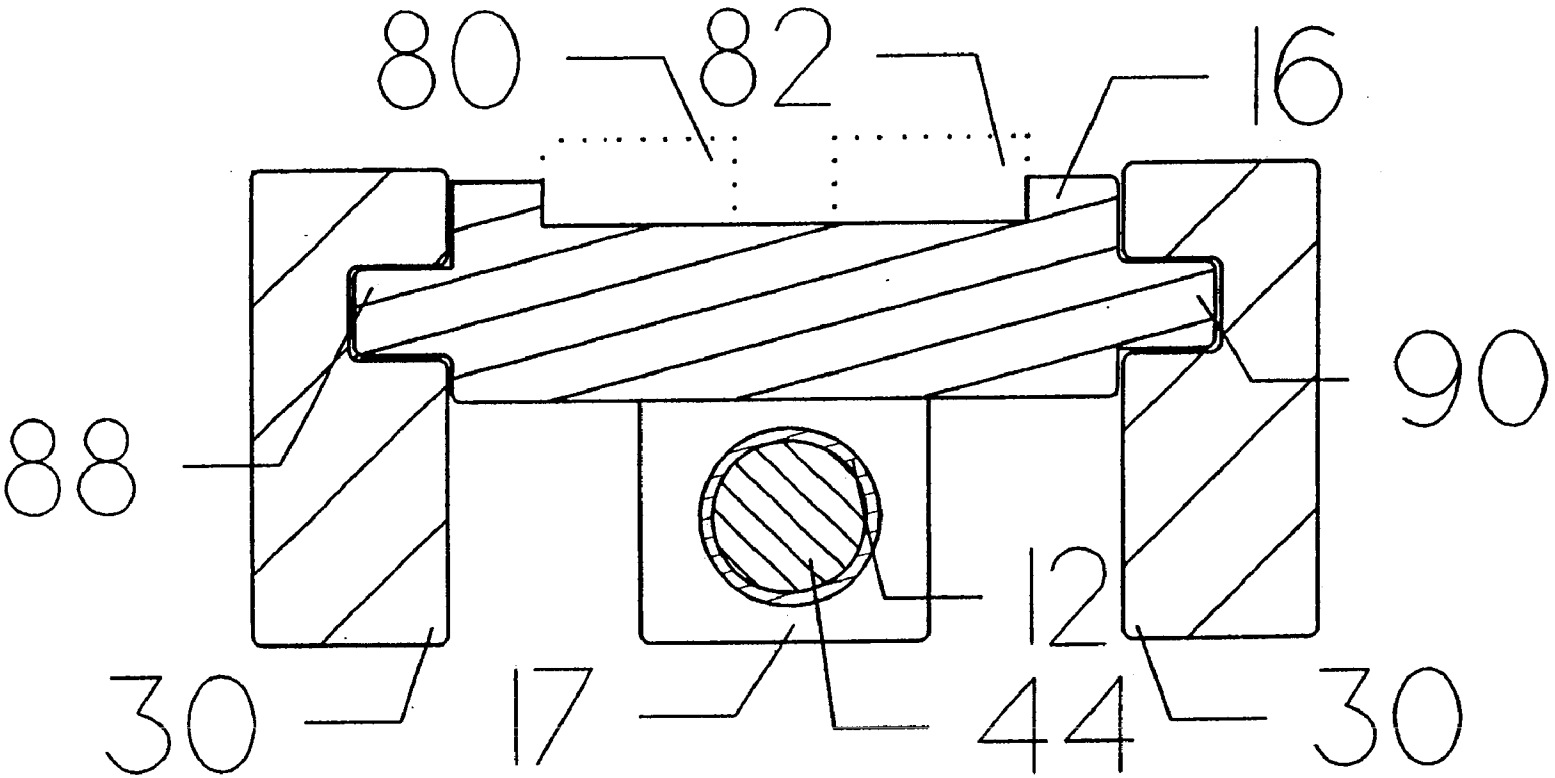
FIG. 8 is a sectioned partial view of the preloading engagement means.

FIG. 8 is a partial sectioned view of preloading engagement assembly 16. Projections 88 and 90 of preloading engagement assembly 16 slide within corresponding recesses within engagement track 30. All other referenced elements are as previously described. Preferably canula 12, stylet 44 and compression spring 32 are fabricated of stainless steel and all other elements are molded of a convenient disposable polymer.

Having thus described the preferred embodiments of the present invention, those of skill in the art will be readily able to apply these teachings to yet other embodiments within the scope of the claims hereto attached, and wherein

I claim:

1. In an apparatus for surgically removing tissue samples of different sizes including, a canula having a central lumen, a stylet slidably mounted within said lumen and having a sample holding notch adjacent a distal end, and a control assembly connected to the canula and the stylet for controlling relative movement between the canula and the stylet during tissue sample removal, the improved apparatus for selecting tissue sample size comprising:

a. a tissue sample size selector means connected to the canula and slidably mounted for axial movement in the control assembly, wherein proximal movement of the selector means causes proximal movement of the canula, *thereby determining subsequent positioning of the cannula* relative to the stylet notch;

b. detent means mounted on the control assembly for releasibly holding the selector means in any one of a plurality of selectable tissue sample size settings;

c. a spring biased against the proximal axial movement of the selector means; and d. manual release means for selectively releasing the selector means from the detent means following placement of the stylet for tissue sample removal, whereby the spring causes distal axial movement of the canula relative to the stylet to cut a tissue sample of a selected size into the notch.

2. An apparatus according to claim 1 wherein said selector means and said detent means cooperate to provide selection of three distinct tissue sample sizes.

3. An apparatus according to claim 1 or 2 wherein the stylet has a distal tip ground in a plane having a lateral projection away from a distal end of the tissue sample notch.

4. In an apparatus for surgically removing tissue samples of different sizes including, a canula having a central lumen, a stylet slidably mounted within said lumen and having a sample holding notch adjacent a distal end, and a control assembly connected to the canula and the stylet for controlling relative movement between the canula and the stylet during tissue sample removal, the improved apparatus for taking tissue samples comprising:

a. a distal tip on the stylet ground in a plane having a lateral projection away from a distal end of the stylet notch.

5. An apparatus according to claim 4 wherein the canula has a distal tip ground within the same plane as the distal tip of the stylet when the stylet and the canula are both maximally advanced distally.

*6. In an apparatus for surgically removing tissue samples of different sizes including, a cannula having a central lumen, a stylet slidably mounted within said lumen and having a sample holding notch adjacent a distal end, and a control assembly connected to the cannula and the stylet for controlling relative movement between the cannula and the stylet during tissue sample removal, the improved apparatus for selecting tissue sample size comprising:*

*a. a tissue sample size selector means connected to the cannula and slidably mounted for axial movement in the control assembly, wherein proximal movement of the selector means causes proximal movement of the cannula, thereby determining subsequent positioning of the cannula relative to the stylet notch;*

*b. detent means mounted on the control assembly for releasably holding the selector means in any one of a plurality of selectable tissue sample size settings;*

*c. a spring biased against the proximal movement of the selector means;*

*d. the stylet connected to the tissue sample size selector means and slidably mounted for axial distal movement independent of axial distal movement of the cannula, without releasing the selector means; and*

*e. manual release means for selectively releasing the selector means from the detent means following placement of the stylet for tissue sample removal, whereby the spring causes distal axial movement of the cannula relative to the stylet to cut a tissue sample of a selected size into the notch.*

* * * * *